United States Patent [19]

Barlett

[11] 4,360,017
[45] Nov. 23, 1982

[54] MOUTHPIECE FOR RESUSCITATION

[76] Inventor: Harry Barlett, 500 Green Rd., No. 803, Stoney Creek, Ontario, Canada, L8E 3M6

[21] Appl. No.: 244,865

[22] Filed: Mar. 18, 1981

[51] Int. Cl.³ .......................................... A61M 16/00
[52] U.S. Cl. ............................ 128/202.28; 128/207.14
[58] Field of Search ...................... 128/202.28, 202.29, 128/203.11, 207.14, 207.12, 277, 203.15, 204.25, 205.11

[56] References Cited

U.S. PATENT DOCUMENTS

| | | | |
|---|---|---|---|
| 1,933,733 | 11/1933 | Hess | 128/204.25 |
| 2,280,050 | 4/1942 | Alexander et al. | 128/203.11 |
| 2,343,231 | 2/1944 | Talley | 128/204.25 |
| 3,006,337 | 10/1961 | Aguado | 128/202.28 |
| 3,013,554 | 12/1961 | Safar et al. | 128/202.28 |
| 3,057,347 | 10/1962 | McGee | 128/202.28 |
| 3,079,916 | 3/1963 | Marsden | 128/202.28 |
| 3,137,293 | 6/1964 | Green | 128/202.28 |
| 3,203,845 | 2/1967 | Detmer | 128/202.28 |
| 3,395,700 | 8/1968 | Stillman | 128/202.28 |
| 3,538,913 | 11/1970 | Stolfi | 128/202.28 |
| 3,802,428 | 4/1974 | Sherman | 128/202.28 |
| 3,998,226 | 12/1976 | Harris | 128/203.15 |
| 4,240,418 | 12/1980 | Rosskamp et al. | 128/203.15 |

FOREIGN PATENT DOCUMENTS 793601 9/1968 Canada ............................ 128/202.28

Primary Examiner—Henry J. Recla
Attorney, Agent, or Firm—Moss, Bensette, Thompson, Squires

[57] ABSTRACT

A rescue breathing device or insufflator is shown for providing mouth-to-mouth artificial resuscitation to a victim of suffocation or asphyxiation. The device has a tubular body comprising an input portion and an output portion. The tubular body has a central axial air passageway converging in cross-sectional area in the input portion to a central venturi region. At least one fresh air port communicates with the venturi region. The air passageway in the output portion diverges or is of constant cross-sectional area, so that a venturi effect is produced when the device is used, resulting in the venturi mixing fresh ambient air with the respirated air provided to an asphyxiation victim by a rescuer, thereby increasing the oxygen content of the air delivered to the victim by the resuscitation process. A shield is removably mounted on the tubular body to provide a good seal and prevent lip contact between the rescuer and the victim.

15 Claims, 7 Drawing Figures

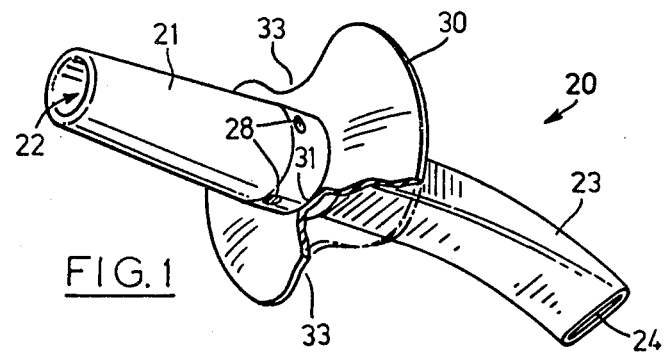
FIG. 1
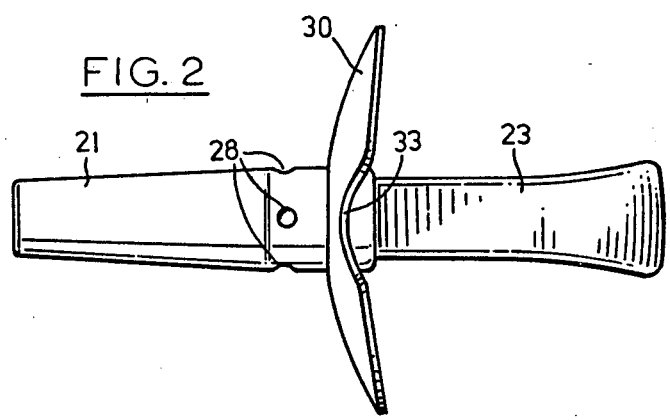
FIG. 2
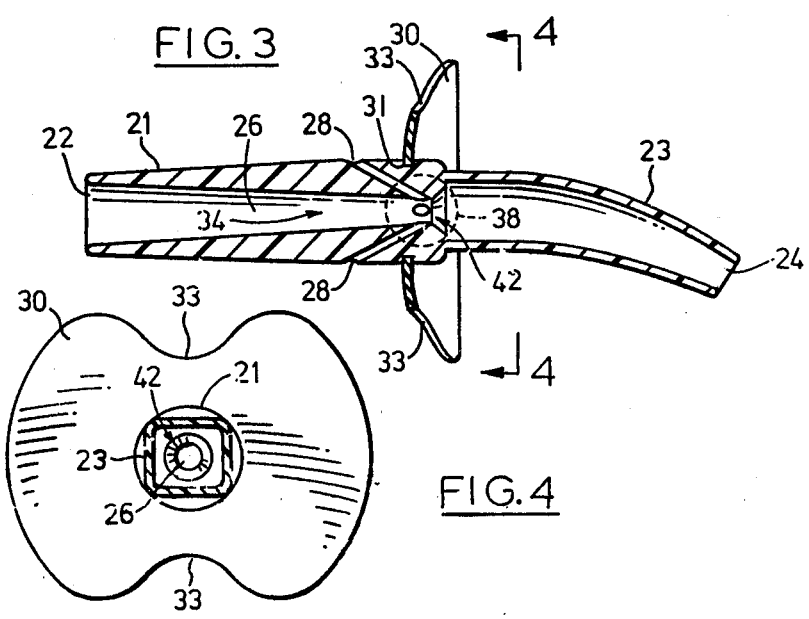
FIG. 3
FIG. 4

MOUTHPIECE FOR RESUSCITATION

BACKGROUND OF THE INVENTION

This invention relates generally to rescue breathing devices and more particularly to devices to be used to provide artificial respiration to victims of suffocation or asphyxiation.

Several problems have characterized mouth-to-mouth resuscitation methods in the past. One problem is the physical contact between the victim of asphyxiation or suffocation and the person attempting to administer mouth-to-mouth resuscitation. For squeamish rescuers, the lip contact between the rescuer and the victim, particularly in cases where the victim has vomited or has food in his mouth, would prove to be a deterrent to the administration of artificial respiration. Unfortunately, it is known that complete oral contact or a good seal between the rescuer's mouth and the victim's mouth is necessary to provide an effective resuscitation of a victim to avoid fatal results.

In addition to the problem of oral contact, other problems exist which may frustrate the efforts of the rescuer in resuscitating the suffocating victim. Related problems are in the common tendency of the victim either to swallow his tongue or to undergo a muscle contraction in the nasal pharynx thereby partially or completely occluding the trachea. These related problems are particularly characteristic of victims of electrocution or drowning.

Another related problem which has been found to occur in efforts to provide a victim of suffocation or asphyxiation with artificial respiration has been the fact that the air delivered to the victim by the rescuer is rich in carbon dioxide and relatively poor in oxygen because the air has been through one breathing cycle of the rescuer. Accordingly, the rescuer's first use of the air before delivery to the rescue victim has caused a decrease in the quality of air delivered to the rescue victim because it has been respirated once by the rescuer.

SUMMARY OF THE INVENTION

The apparatus disclosed herein is a novel mouthpiece or rescue breathing device which finds application to the resuscitation of victims through use of the mouth-to-mouth resuscitation method. The device provides a breathing apparatus which is helpful in overcoming the problems set forth hereinabove.

The apparatus disclosed herein provides a rescue breathing device which may be shaped and constructed to avoid any undesirable direct contact of the mouths of the victim and the rescuer, and which additionally is helpful to prevent the victim from swallowing his tongue or otherwise from having his trachea obstructed or occluded.

The mouthpiece of this invention is arranged and constructed so as to permit the respirated air provided to the asphyxiation victim by the rescuer to have an enhanced oxygen level due to mixing of the respirated air with ambient air.

According to the invention, there is provided an insufflator for administering resuscitation comprising an elongate member having an input portion and an output portion and a central axial air passageway passing therethrough. The air passageway has a venturi region at the junction of the input and output portions. The air passageway in the input portion decreases in cross-sectional area toward the venturi region. The elongate member defines at least one fresh air port communicating with the venturi region. Also, the air passageway in the input portion and the venturi region are dimensioned to produce a venturi effect when air is blown into the input portion to draw ambient air through the fresh air port into the air passageway.

BRIEF DESCRIPTION OF THE DRAWINGS

A preferred embodiment of the invention will now be described, by way of example, with reference to the accompanying drawings, in which:

FIG. 1 is a perspective view of a preferred embodiment of an insufflator according to the present invention;

FIG. 2 is a top plan view of the insufflator shown in FIG. 1;

FIG. 3 is a vertical cross-sectional view of the embodiment of FIG. 1 showing the axial air passageway passing through the insufflator;

FIG. 4 is a cross-sectional view taken along lines 4—4 of FIG. 3;

DETAILED DESCRIPTION OF THE PREFERRED EMBODIMENT

Figure 5:
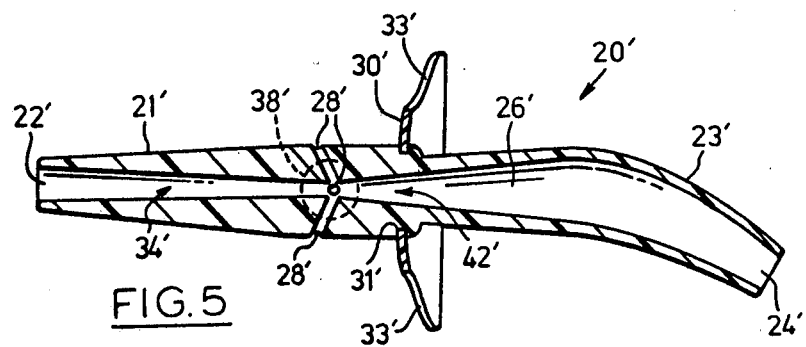
FIG. 5 is a vertical cross-sectional view similar to FIG. 3 showing an alternative embodiment of the insufflator of this invention.

Reference is first made to FIGS. 1 to 4 which show an insufflator for administering resuscitation indicated generally by reference numeral 20. The insufflator 20 is an elongate device having a tubular body comprising an input portion 21 and an output portion 23. Input portion 21 has an inlet opening 22 at one end thereof, and output portion 23 has an outlet opening 24 at the distal end thereof. An axial air passageway 26 runs between inlet opening 22 and outlet opening 24. The cross-sectional area of air passageway 26 inside output portion 23 is generally constant. Output portion 23 is curved and transversely diverging toward outlet opening 24 as seen best in FIGS. 1 and 2, the purpose of which is described further below. The cross-sectional area of air passageway 26 inside input portion 21 decreases from inlet opening 22 toward the centre of insufflator 20. Input portion 21 is generally cylindrical in shape. Fresh air ports 28 are shown approximately mid-way along the tubular body of insufflator 20 through which ambient air may be drawn to mix with the air passing along the air passageway 26 provided in the interior of the insufflator body, because the central part of air passageway 26 forms a venturi, as described further below.

A shield 30 is removably mounted on the tubular body of insufflator 20 as shown in cut-away in FIG. 1. Shield 30 is concave toward the distal end of output portion 23 and is constructed of a pliable or flexible plastic material. The tubular body of insufflator 20 is constructed of a relatively rigid plastic material, thereby permitting the removal of shield 30 for storage, packaging, etc. Shield 30 is normally not mounted on the tubular body of insufflator 20 when not in use, so that when the insufflator 20 is taken from its package to be used to apply artificial resuscitation to an asphyxiation victim, shield 30 may be slipped over input portion 21 to be located in an annular groove 31 formed in the input portion 21 of insufflator 20 adjacent to fresh air ports 28. Shield 30 has peripheral indented portions 33, one of which is to accommodate a victim's nose, should this interfere with the insertion of insufflator 20 into the victim's mouth.

Referring in particular to FIG. 3, respirated air entering inlet opening 22 passes along air passageway 26 until it enters the central part of air passageway 26 shown generally by dotted circle 38 and referred to herein as the venturi region 38. It will be noticed that air passageway 26 is converging from inlet opening 22 toward venturi region 38. This part of air passageway 26 is referred to as the converging portion 34. Also, air passageway 26 expands or diverges in venturi region 38 just prior to output portion 23 of insufflator 20. This latter part of air passageway 26 is referred to as the diverging portion 42, wherein the cross-sectional area of the air passageway therein increases in a direction away from venturi region 38. It will be appreciated that converging portion 34 and diverging portion 42 of air passageway 26 from a venturi in accordance with Bernoulli's principles. This results in low or decreased static pressure in venturi region 38 as air is blown through air passageway 26 from inlet opening 22 to outlet opening 24. The decreased static pressure in venturi region 38 causes ambient air to be drawn into each fresh air port 28 to mix with the air passing through air passageway 26. In this way, insufflator 20 acts something like an ejector or aspirator pump. The prime consideration to the creation of a venturi effect in region 38, is that the gas passing therealong has a sufficiently high velocity that its static pressure is less than the static pressure of the ambient air, particularly the ambient air in the vicinity of the inlets of fresh air ports 28.

In operation, the rescuer will place the curved output portion 23 of the insufflator into the victim's mouth ensuring that the tongue or other obstructions contained in the victim's mouth will not interfere with the passage of air into the victim's trachea. Shield 30 rests against the victim's mouth to provide a good seal and prevent lip contact between the rescuer and the victim. The rescuer places his lips over the inlet opening 22 of input portion 21 and blows his respirated air into inlet opening 22. The fresh air drawn into air passageway 26 in the vicinity of venturi region 38 is mixed in the area of diverging portion 42 adjacent to venturi region 38 with the respirated air blown into insufflator 20 by the rescuer. Thereafter, the respirated air and the ambient air mixed therewith passes along the part of air passageway 26 in output portion 23, and is discharged into the victim's trachea at the outlet opening 24 of the air passageway. In this fashion, respirated air mixed with oxygen rich ambient air is provided to an asphyxiation victim.

FIG. 5 shows an alternative embodiment of the shape of the air passageway 26' provided within the insufflator 20'. Primed reference numerals are used in FIG. 5 to indicate parts similar to those of the embodiment of FIGS. 1 to 4. As may be seen, the cross-sectional area of the air passageway 26' gradually decreases from inlet opening 22' until it reaches a minimum cross-sectional area in the vicinity of venturi region 38'. The cross-sectional area of the air passageway 26' also gradually increases from venturi region 38' until it reaches a cross-sectional area at least equal to that of outlet opening 24'. The gradual reduction in cross-sectional area of the air passageway between inlet opening 22' and venturi region 38' ensures that the air passing along the air passageway 26' increases in velocity as the cross-sectional area decreases thereby rendering a maximum velocity in the vicinity of the venturi region 38'. As previously explained, the higher the air velocity in the vicinity of venturi region 38', the lower the static pressure in this region, and accordingly, the higher the pressure differential appearing across fresh air ports 28' causing ambient air to be drawn into the inlet openings of fresh air ports 28' to produce the desired venturi effect as described above. It will be noticed that there are not only two fresh air ports 28' in insufflator 20', as opposed to four ports in insufflator 20.

As can be seen in both FIGS. 3 and 5, the fresh air ports 28, 28' are slightly inclined from perpendicular to the air passageways 26, 26'. This inclination of the fresh air ports 28, 28' helps ensure that ambient air drawn into the air passageways and mixed with the respirated air passing along air passageways 26, 26' has a velocity component directed toward outlet openings 24, 24', thus reducing flow losses. Although the fresh air ports 28, 28' may be perpendicular to air passageway 26, 26', including the fresh air ports 28 in the fashion referred to above helps enhance the amount of ambient air drawn into the air passageways as well as the mixing of the ambient air and the respirated air downstream from the venturi region, namely in the region generally depicted by reference numerals 42, 42'.

Figure 6:
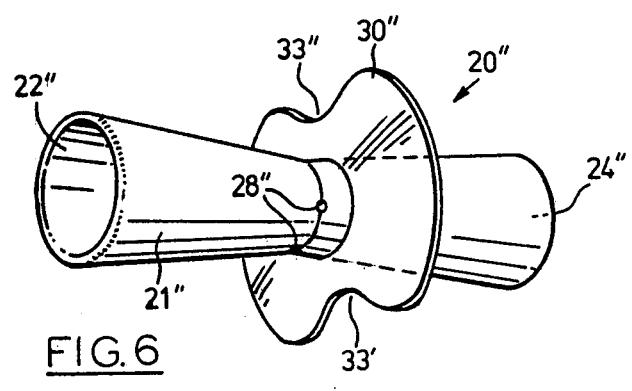
FIG. 6 is a perspective view of yet another embodiment of the insufflator according to this invention.
Figure 7:
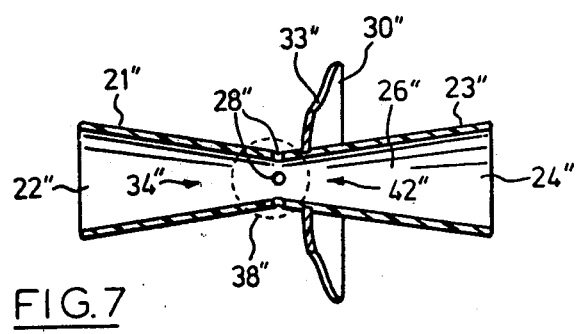
FIG. 7 is a vertical cross-sectional view of the embodiment of FIG. 6 showing the internal air passageway passing therethrough.

Referring next to FIGS. 6 and 7, another embodiment of an insufflator for administering resuscitation is shown. This embodiment of the insufflator contains similar features to the embodiments described previously, and double primed reference numerals are used to refer to similar parts of this embodiment.

This embodiment of the invention shows an inlet opening 22" which has a longer cross-sectional area and an air passageway 26" that generally decreases until a minimum cross-sectional area is reached at the venturi region 38" of the air passageway 26" formed in insufflator 20". Thereafter, the cross-sectional area of the air passageway increases until it is a maximum at the outlet opening 24". As may be appreciated, this embodiment of the insufflator is not as advantageous as the embodiment shown in FIGS. 1 to 4, because the shape of the output portion 23" in contact with the victim's mouth will not allow the output portion 23" to be located past the nasal pharynx region of the asphyxiation victim. However, this embodiment of the insufflator will work effectively provided there is not an occlusion of the trachea owing to contration of the victim's muscles in the nasal pharynx region.

While in the foregoing specification, there has been set forth a detailed description of the preferred embodiments of the invention, it should be understood that the descriptions relating to the preferred embodiments were for the purpose of illustration only. It will be appreciated by those skilled in the art that many changes in the details of the construction given may be made without departing from the spirit and the scope of the invention as described in the appended claims. For example, the shapes and dimensions of input portions 21, 21' and 21", and output portions 23, 23' and 23" could be varied as desired, as long as the venturi effect is produced to draw in fresh air as air is blown through the insufflator. In particular, output portions 23, 23' and 23" could be cylindrical, as opposed to curved or conical, especially if it is desired to mold the tubular body of the insufflator as one piece. Further, although two or four fresh air ports 28, 28', 28" are described above, it will be appreciated that only one fresh air port could be used, if desired. Finally, the shield indented portions 33 could be eliminated if desired.

What I claim as my invention is:

1. An insufflator for administering resuscitation comprising:
    an elongate member having an input portion, a central portion and an output portion and a central axial air passageway passing therethrough; said input portion defining input mouthpiece means into which air can be blown by a person administering the resuscitation, said output portion defining output mouthpiece means insertable into the mouth of a recipient; the air passageway having a venturi in said central portion; the air passageway in the input portion decreasing in cross-sectional area toward the venturi; the elongate member defining at least one fresh port communicating with the throat of said venturi; and the air passageway in the input portion and venturi being dimensioned to produce a venturi effect when air is blown into the input portion to draw ambient air through the fresh air ports into the air passageway.

2. An insufflator as claimed in claim 1 wherein the air passageway in the output portion is of generally constant cross-sectional area.

3. An insufflator as claimed in claim 2 wherein the output portion is curved and transversely diverging in a direction away from the venturi.

4. An insufflator as claimed in claim 2 and further comprising a flexible shield removably mounted on the elongate member between the fresh air port and the distal end of the output portion of the elongate member, the shield being located adjacent to the fresh air port.

5. An insufflator as claimed in claim 2 and further comprising a flexible shield removably mounted on the elongate member between the fresh air port and the distal end of the output portion of the elongate member, the elongate member defining an annular groove located adjacent to the fresh air port for accommodating and retaining the shield in position.

6. An insufflator as claimed in claim 2 and further comprising a flexible shield removbly mounted on the elongate member between the fresh air port and the distal end of the output portion of the elongate member, the shield being concave toward the distal end of said output portion.

7. An insufflator as claimed in claim 2 and further comprising a flexible shield removably mounted on the elongate member between the fresh air port and the distal end of the output portion of the elongate member, the shield defining a peripheral indented portion for accommodating the nose of a victim.

8. An insufflator as claimed in claim 1 wherein the cross-sectional area of the passageway in the output portion increases in a direction away from the venturi.

9. An insufflator as claimed in claim 8 wherein the output portion is curved and transversely diverging in a direction away from the venturi.

10. An insufflator as claimed in claim 8 and further comprising a flexible shield removably mounted on the elongate member between the fresh air port and the distal end of the output portion of the elongate member, the shield being located adjacent to the fresh air port.

11. An insufflator as claimed in claim 1 and further comprising a flexible shield removably mounted on the elongate member between the fresh air port and the distal end of the output portion of the elongate member.

12. An insufflator as claimed in claim 11 wherein the shield is concave toward the distal end of said output portion.

13. An insufflator as claimed in claim 11 wherein the shield defines a peripheral indented portion for accommodating the nose of a victim.

14. An insufflator as claimed in claim 1 wherein the fresh air port is inclined transversely of the central axial air passageway, so that the ambient air entering the central air pasageway from the fresh air port has a velocity component toward the output portion of the elongate member.

15. An insufflator as claimed in claim 1 comprising a plurality of said fresh air ports.

* * * * *